United States Patent
Rodriguez

[11] Patent Number: 5,411,494
[45] Date of Patent: May 2, 1995

[54] SPONGE BATH MACHINE AND METHOD FOR USING

[76] Inventor: Victorio C. Rodriguez, 7791 Hoertz Rd., Parma, Ohio 44134

[21] Appl. No.: 126,929

[22] Filed: Sep. 27, 1993

[51] Int. Cl.$^6$ ............................................. A61M 35/00
[52] U.S. Cl. .................................. 604/290; 604/291; 604/305; 5/421; 607/85; 165/46
[58] Field of Search ............................. 607/81, 83–87, 607/104; 604/289, 290, 291, 304, 305; 62/259.3; 165/46; 2/81, 97, 102, 108; 239/289; 5/421; 405/36; 47/79 CR, 62

[56] References Cited

U.S. PATENT DOCUMENTS

| | | | |
|---|---|---|---|
| 3,431,565 | 3/1969 | Nelson | 4/598 |
| 3,997,927 | 12/1976 | Culligan | 5/421 X |
| 4,144,620 | 9/1978 | Moore et al. | 607/104 |
| 4,211,037 | 7/1980 | Green | 47/62 X |
| 4,245,434 | 1/1981 | Green | 47/62 X |
| 4,648,143 | 3/1987 | Breaux et al. | 239/289 X |
| 5,027,455 | 7/1991 | Commisso et al. | 5/421 |
| 5,146,633 | 9/1992 | Kim et al. | 5/421 |
| 5,165,127 | 11/1992 | Nicholson | 5/421 |
| 5,259,379 | 11/1993 | Kim et al. | 607/104 |
| 5,269,369 | 12/1993 | Faghri | 607/104 |
| 5,300,103 | 4/1994 | Stempel et al. | 604/291 |
| 5,320,164 | 6/1994 | Szczesuil et al. | 165/46 |

FOREIGN PATENT DOCUMENTS

| | | | |
|---|---|---|---|
| 1144438 | 2/1963 | Germany | 607/104 |
| 85003216 | 8/1985 | WIPO | 607/104 |

*Primary Examiner*—Mary Beth O. Jones
*Attorney, Agent, or Firm*—Donald A. Bergquist

[57] ABSTRACT

A therapeutic method for treating hypothermia and hyperthermia conditions in human patients by applying a continuous flow of temperature-controlled warmed water over a substantial area of the body of the patient to effect sensible heat transfer between the body and the water. Apparatus is provided for warming, delivering, and distributing the water flow over at least fifty percent of the patient's body and for collecting spent water into a receptacle. A network of water-permeable tubes delivers a flow of warmed water to an absorbent web draped over the body of the patient, thereby to distribute the water flow over a large area and in close proximity to and wetting the surface of the patient's body, thereby to effect sensible heat transfer over a large area. Evaporative heat loss may be minimized by reducing air convection adjacent the water flow.

19 Claims, 2 Drawing Sheets

SPONGE BATH MACHINE AND METHOD FOR USING

INTRODUCTION

This disclosure relates to a method and equipment therefor to provide treatment for health care patients suffering from either acute hypothermia (excessively depressed body temperature) or acute hyperthermia (excessively elevated body temperature). The disclosure especially addresses conditions where the thermia condition (a non-standard term used here to refer to either or both hypothermia and hyperthermia) is a manifestation or symptom of an abnormal medical condition or where the thermia condition is accompanied by another abnormal medical condition. In particular it addresses the situation wherein prudent treatment of such abnormal medical condition contraindicates the use of drug therapy to achieve normal body temperature or to achieve normal body temperature without the use of drugs.

BACKGROUND

At the outset, one should appreciate that, even in the health care field, where clarity may be crucial, confusion may exist in terminology in cases where similar words are used to refer to opposite conditions and or treatments. Whether this is due to a lack of knowledge, to carelessness, or to a different intent in meaning is immaterial. For our purposes, whe shall adhere to the following, which we believe to be standard nomenclature. Hypothermia is a condition of depressed or subnormal body temperature; hypothermia may be treated by using medication or it may be treated by exposing the patient to a hyperthermic (warmer than normal body temperature) environment. Some might refer to the latter treatment as hyperthermia, but we caution to avoid this usage. Hyperthermia is a condition of elevated body temperature; hyperthermia may be treated by using medication or it may be treated by exposing the patient to a hypothermic (cooler than normal body temperature) environment. Some might refer to the latter treatment as hypothermia, but we caution also to avoid this usage.

The use of external cooling means to treat patients with fever (or hyperthermia) is not new. U.S. Pat. No. 1,004,192, issued in 1911 to J. T. Phelan, teaches a cooling apparatus comprising a coolant-filled cooling pipe with closed ends connected to an elevated receptacle for liquid coolant and ice. The pipe is placed adjacent to the body and especially underneath the neck and surrounding the head of the supine patient. As the coolant in the pipes becomes warm, it will be replaced by cold coolant. Although Phelan does not discuss a motive force by which the warm coolant is replaced by cold coolant, his disclosure suggests that thermal convection currents are expected to accomplish this end. In contrast to the present invention, Phelan makes no suggestion that the liquid is not fully contained within the apparatus.

Along a similar vein, F. C. Hoore et el, in U.S. Pat. No. 3,867,939, issued in 1975, teaches a temperature-controlled applicator pad. A circuit of passages within this pad allows a thermal fluid to circulate into the pad, through a serpentine pattern of passages, and out of the pad in a forced circulation. Although the pad may be wetted, preferably with a sterile solution, to improve the heat transfer characteristics of the soft, absorbent, flexible covering, the thermal fluid is not the source of such wetting. In contrast to Moore, the present invention does not define a closed circuit for the flow of a thermal fluid; rather, the fluid water—is distributed to an absorbent sheet that provides yet greater dispersion of the water for contact with the skin of the patient, ultimately to be drained off to a receptacle for spent water.

Another such device for forced circulation of a thermal fluid through a fluid-tight circuitous path is presented in U.S. Pat. No. 4,996,145, issued in 1990 to M. Kikumoto et el. Designed primarily for use on wheelchairs and primarily for cooling the body of the wheelchair occupant, it teaches a pump cirulating a thermal fluid that is chilled by refrigeration.

U.S. Pat. No. 4,572,188, issued in 1986 to S. D. Augustine et el., teaches apparatus for controlling body temperature by means of a temperature-controlled gas mixture (usually air) supplied to an inflatable cover through which it circulates and which also serves as a plenum or manifold to transmit the temperature controlled gas to the body surfaces, thereby to thermally bathe the body in the gas. Because of the low volumetric heat capacity (measured in BTU/cu ft/degree F. or in Calories/liter/degree C.) of gases in general, and air in particular (about 1/3300 times that of liquid water), relatively large volumes of temperature-controlled gas are required to achieve the same effect of a quantity of water. The venting of the temperature-controlled gas in large quantity into the room in which the patient is being treated will thermally bathe the entire room and its other occupants in the temperature-controlled gas mixture. In contrast, the present invention uses water as a thermal medium; the use of water as a medium has little effect on the atmosphere in the room, largely because the spent water can be contained and does not present itself to other people in the room.

In U.S. Pat. No. 3,247,851, issued in 1966 to M. J. Seibert, an apparatus is taught for applying sustained moist heat to a human body by using an electrical heating jacket on an inverted bottle of a type commonly used for parenteral solutions, thereby to heat the liquid within, which is then applied by means of a drip line to moisten and to maintain an elevated temperature of a pad of adsorbent material. For extended moist heat treatment, unheated bottles may be connected in a series arrangement as may be commonly used for other purposes, but with the heated bottle being the final reservoir in the series.

SUMMARY OF THE INVENTION

The present invention will be seen as different from the prior art discussed above. The present invention relates to treatment of either hypothermia or hyperthermia using much the same method.

Applicant is not so naive as to believe that treating fever cases by administering a simple sponge bath with tepid water or even with alcohol or alcohol-water mixtures is new or novel medicine. One must realize, however, that administering such treatement is labor intensive. It is desirable, therefore, to provide a method and equipment therefor that offers effective treatment for a thermia condition without the constant presence of an attending nurse or aide.

The efficacy of this treatment has been tested, at least on a small scale. In a hospital that admitted 51 patients with simple pneumonia (including fever—i.e., hyperthermia) during the six-month period from July 1992 through December 1992, the average hospital stay for patients who were treated using conventional anti-pyretic drug therapy for fever (in addition to the usual intravenous fluids, oral fluids, and antibiotics) was $6\frac{1}{8}$ days (n=48; s=2.74). Three of the simple pneumonia patients were treated with a modified form of the present invention (in addition to the usual intravenous fluids, oral fluids, and antibiotics) and their average hospital stay was 3 days (n=3; s=1.00). Applying a statistical test of significance (the t-test) reveals that there is a 97-percent probability that the samples are representative of two distinct populations. That is to say, there is a 97-percent certainty that the tested treatment had an effect on the length of hospital stay. There may be bias in this result in that the doctor treating the three patients, he who decides upon whether the patient in the test sample (n=3) can be discharged from the hospital, is also the inventor, but the reported study is only a preliminary study to determine whether a patent should be pursued. It should not be considered as medical proof of efficacy.

Applicant believes that sponge bath therapy performs better than anti-pyretic drug therapy because, as is known, anti-pyretic drugs lower body temperature by inhibiting prostaglandins. Prostaglandins play a critical role in the immune response and other defensive mechanisms that are activated in the defense of the body against infection, so it is reasoned that inhibiting them is counterproductive to the healing process. Conventional sponge bath therapy for fever is not commonly used because it is labor intensive and is therefore used only in cases of extreme emergency.

It is an object of this invention to provide a treatment method that is therapeutically effective in treating both hypothermia and hyperthermia and comprising delivering and distributing to a large portion (at least 50%) of the surface of the body of a thermia patient a controlled flow of water at a temperature at or near that of the normal human body.

It is an object of this invention to provide apparatus for a treatment method that is therapeutically effective in treating both hypothermia and hyperthermia, which apparatus comprises equipment for delivering and distributing to a large portion (at least 50%) of the surface of the body of a thermia patient a controlled flow of water at a temperature at or near that of the normal human body.

It is a further object of this invention to provide such apparatus comprising a water supply, a water heating means, a thermostat controlling said water heating means, a flexible tube to carry temperature-controlled water to the proximity of said patient, a system of water-permeable water distribution tubes supplied with temperature-controlled water from said flexible tube to distribute water over an area of an absorbent web that further distributes water throughout the extent thereof and thereby to an extensive area of the surface of the body of said patient over which said web is draped, thereby to make good thermal contact between said flowing water and said patient.

It is a furher object of this invention that said apparatus also comprise an underlayment upon which said patient is placed, which underlayment will collect by gravity excess water delivered to the body of the patient and to direct said excess water into a spent water receptacle.

It is yet another object of this invention to provide a specific embodiment of the apparatus wherein said water source is a refillable reservoir that is elevated with respect to the patient, thereby to provide for water flow by the action of gravity alone.

It is yet another object of this invention to provide a specific embodiment of the apparatus wherein said water source is a refillable reservoir and wherein water flow is provided by a pump means.

It is yet another object of this invention to provide a specific embodiment of the apparatus wherein said water source is a water tap connected to the water supply for a building.

It is yet another object of this invention to provide a specific embodiment of the apparatus wherein said water-permeable water distribution tube is a flexible tube having discrete holes through the wall thereof and spaced along the length thereof.

It is yet another object of this invention to provide a specific embodiment of the apparatus wherein said water-permeable water distribution tube is a flexible tube having a substantially uniformly porous wall.

It is yet another object of this invention to provide a specific embodiment of the apparatus wherein said water-permeable water distribution tube is attached to a web or sheet that holds said tube in position when draped over said patient.

It is yet another object of this invention to provide a specific embodiment of the apparatus wherein said tube-holding web is separate from said absorbent web that is draped over said patient.

It is yet another object of this invention to provide a specific embodiment of the apparatus wherein said separate tube-holding web is substantially non-permeable, thereby to prevent substantial evaporative cooling of the water applied to the patient.

It is yet another object of this invention to provide a specific embodiment of the apparatus wherein said tube-holding web is also the absorbent web that is draped over said patient.

These, and other objects of this invention, will become abundantly clear to the reader in the following detailed description of the invention.

DETAILED DESCRIPTION OF THE INVENTION

This invention will be most easily understood by referring to the attached drawings, wherein parts are identified by reference numbers consistent with the following description. In each view, the same part carries the same reference number.

Figure 1:
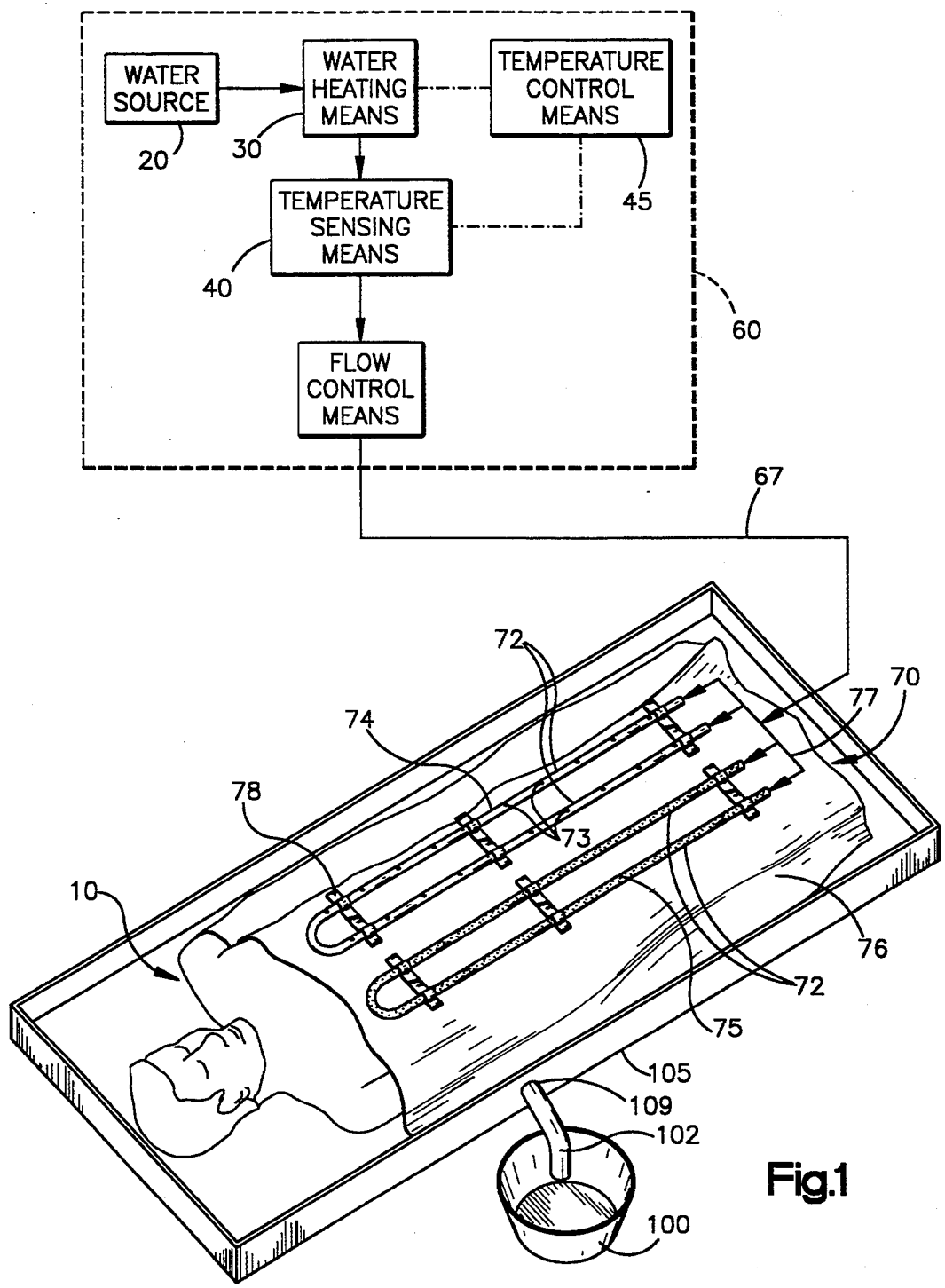
FIG. 1 illustrates in symbolic form, the process of this invention.

The overall process is illustrated in FIG. 1, in a combined format of isometric drawing and block diagram. FIG. 1 shows a patient 10 being treated by using the process of this invention. The process begins with a water source 20. This source could be a water tap, an elevated refillable vessel, or a refillable vessel with an associated water pump. All of these possible sources are well known and not novel in and of themselves.

A water heating means 30 is capable of raising the temperature of incoming water passing therethrough. This water heating means could be a reservoir with an associated heat-supplying means, as an electric heater for example. It could also be a heat exchanger to transfer heat from another fluid at elevated temperature. It could also be a water conduit (tube or tubing) with an associated heating element to add heat to the water as it flows through the conduit. All of these heating means are well known and not novel in and of themselves.

A temperature measuring means 40 senses the temperature of the water that exits the water heating means 30 and provides a signal to an adjustable temperature control 45 that modulates the heat input to the water heating means 30, thereby to control the temperature of the flowing water. Such means for temperature control are well known and not novel in an of themselves.

An adjustable flow control means 50 provides a means for controlling the flow of water from the water source 20 and through the water heating means 90 and to the distribution system described below. This control could be a simple valve, such as a needle valve or a globe valve; it could be another adjustable restrictor, such as a roller clamp on flexible tubing or other means to constrict flexible tubing; it could be a more complex device, such as an adjustable motoring pump or a fluid flow control device that provides a constant pressure drop across a constant (although adjustable) flow restrictor. All of these devices are well known and not novel in and of themselves.

The above-described elements may be referred to in total as a source of temperature-controlled water at a pro-selected temperature and flow rate. For brevity, we shall call this warm water source 60.

Water from the warm water source 60 flows through a flexible tube 67 to a distribution system 70. The distribution system 70 comprises a water-permeable tube 72 and an absorbent web 76. Plural water-permeable tubes may be present, along with a manifold 77 to connect them to the flexible tube 67.

The absorbent web 76 may be of any absorbent material. Preferred embodiments include a web of cotton flannel or cotton terrycloth, each of which could be ashed for re-use. Alternatively, a nonwoven fabric or paper sheet having sufficient strength when wetted could be used to provide a less expensive, disposable water distribution web. Experience has shown that cotton flannel or terrycloth without the sizing that is often present on newly-manufactured fabrics, is to be preferred for the absorbent web 76; thus, it may be most desirable to use pre-washed cotton materials for the web 76.

Paper sheeting similar to highly-absorbent paper towels is the preferred disposable material. Currently, a paper towel product with the brand name "BOUNTY" appears to have superior wetting and water distribution properties that would make it an especially suitable material for this application. BOUNTY is a trademark owned by Procter & Gamble Company, of Cincinnati, Ohio, and is applied to paper towels especially noted for their high absorbency.

The water-permeable tubing 72 may be solid-walled tubing having holes 73 piercing the wall at spaced-apart intervals as indicated at 74. Naturally these holes must not be so large as to allow unrestricted flow of the water from them. Rather, they must present sufficient restriction to flow to provide for uniform flow from all holes along the length of the tubing. These holes will "weep" drops of water that will be further distributed by the water-absorbent web 76.

Alternatively, the tubing may be porous-walled tubing wherein the material of which the tubing is made has a porosity that allows flow through the walls, as is indicated at 75. Materials of the latter type are in use as "soaker hoses" for use in watering one's lawn or garden. Some experimenting may be necessary to determine the proper degree of porosity.

FIG. 1 shows the water-permeable tubing attached to the absorbent web 76, in this instance at specific points, examples of which are referenced as 78. Attachment may be made by means of fabric loops sewn onto the web and through which the tubing is threaded, for example.

Whereas when water is distributed over an extended surface as is done in this process, evaporative cooling can take place; as water evaporates (into the atmosphere) it reduces the temperature of the surface it leaves. In this use, such evaporative cooling could create excessive cooling of the skin of a hyperthermia patient, thereby giving the patient 10 a chill, which effect would be undesirable. It is considered prudent, therefore, to provide a non-wetting covering 90 (shown in FIG. 2) over the absorbent web 76, thereby to reduce, if not eliminate evaporative cooling.

Figure 2:
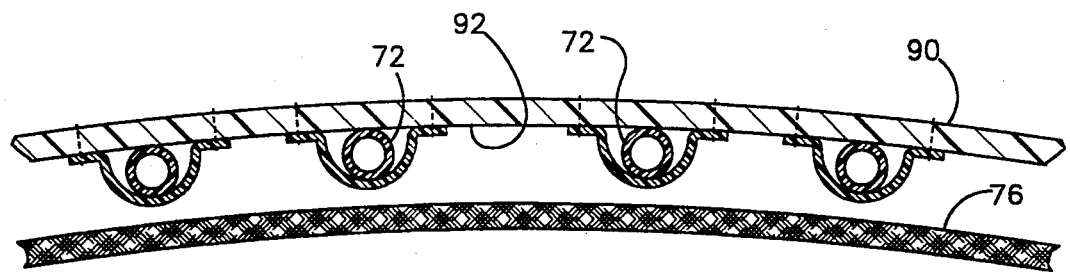
FIG. 2 illustrates an alternate embodiment of a portion of this invention relating to the distribution of water.

FIG. 2 illustrates an alternative embodiment of the retaining of the water-permeable tubing. In this case, the water-permeable tubing 72 is attached to the undersurface 92 of the non-wetting covering 90 that serves to reduce or eliminate evaporative cooling. Attachment may be made by means of fabric loops sewn onto the covering and through which the tubing is threaded, for example. The non-wetting covering 90 covers the the absorbent web 76, and the flowing water from the water-permeable tubing 72 wets the absorbent web 76.

Evaporative cooling is counterproductive when hypothermia is being treated by the administering of warm water over the body. In such cases, evaporative cooling should be minimized.

When evaporative cooling is eliminated, the effect of the use of this invention is dependent upon what is technically called sensible heat transfer only. Sensible heat transfer depends upon a decrease in temperature of the heat source and an increase in the temperature of the colder object. Heat always flows from the warmer to the colder. When hypothermia is being treated, the heat source is the flowing warm water and the colder object is the hypothermia patient. In practice the water temperature to be used is very near to that of the normal human body. When hyperthermia is being treated, the heat source is the hyperthermia patient and the colder object is the flowing water, which is pre-warmed to a temperature sufficiently high to prevent patient chilling that would result in discomfort. In practice the water temperature to be used is, again, very near to that of the normal human body.

Because the major effect being utilized in this invention is the transfer of sensible heat, evaporation of the flowing water will usually be inhibited. The spent water will surround the patient in the bed and should be controlled to prevent soaking the bedding, soaking the mattress, and wetting the floor to create a hazzard. An embodiment of this invention therefore includes, in combination with the water supply and distribution system, a spent water collection system.

The spent water collection system of the best mode, shown in FIG. 1 comprises a spent water receptacle 100, that receives water from a drain line 102 connected to what has been described as a portable bathtub 105 for bedridden patients. This water collection system is similar in general appearance to that taught in U.S. Pat. No. 3,733,620, "COLLAPSIBLE BED SHAMPOO BASIN WITH THROW AWAY LINER," issued in 1973 to G. E. Glintz, although the water collection system of the best mode of the present invention has features not shown in that particular patent. Other collapsible tubs for use on beds include U.S. Pat. No. 4,958,389, "PORTABLE/DISPOSABLE SHOWERBATH," issued in 1990 to R. H. Hammett, and U.S. Pat. No. 4,785,486, "COLLAPSIBLE BATHTUBE," issued in 1988 to E. A. Viesturs. Other similar art of which Applicant is not aware may appear more relevant and is likely to be found in Class 4 (BATHS, CLOSETS, SINKS AND SPITTOONS) in the U.S. Patent Office Classification System.

Figure 3:
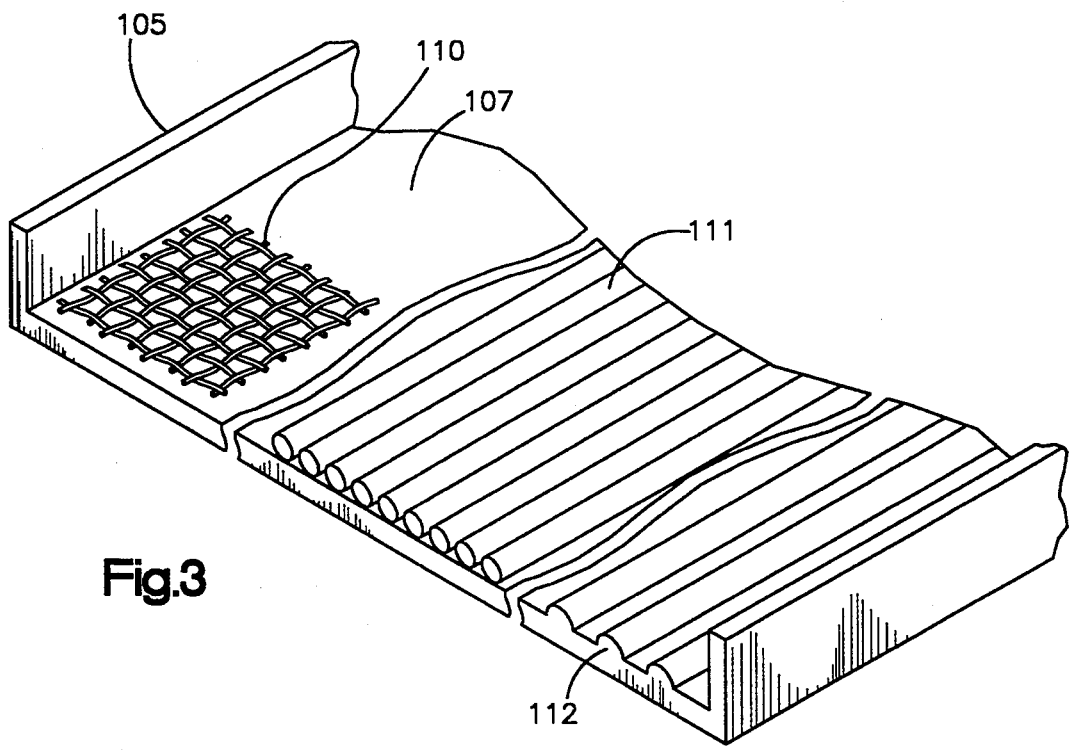
FIG. 3 illustrates several ways to permit draining of spent water from beneath the patient.

It is considered preferable that the patient be supported slightly above the inside surface 107 of the portable bathtub 105 so that his body will not inhibit the flow of water to the drain 109. This result may be effected by any one of several methods, none of which is particularly inventive. These are shown in FIG. 3. A mat 110, either woven or non-woven, of fibers that cross over one another, thereby providing porosity in directions perpendicular to the thickness thereof while providing suitable support, would serve this purpose if it is placed on the inside surface 107 of the tub 105. A similarly-placed mat 111 of flexible reed-like elements all aligned in one direction, similar to a bamboo window shade, may also serve this purpose in satisfactory fashion. Alternatively, the inside surface 107 may be of sufficient roughness as a result of a step in the manufacture thereof, to provide the combination of patient support and spent water flow channels, as is shown at 112, In and of themselves, none of the devices illustrated in FIG. 3 appears to have patentable novelty, but are elements of preferred embodiments of this invention, so they are presented as a part of this disclosure.

I claim:

1. A therapeutic treatment method for use in treating a thermia condition in a human patient, which method comprises mechanically delivering and distributing to more than fifty percent of the surface of the body of said human patient, by means of an absorbent web for said distributing, a substantially continuous controlled flow of water at a controlled temperature that approximates the temperature that is considered normal in a human body, whereby said flow of water effects sensible heat transfer between said water and said human patient, thereby to ameliorate said thermia condition.

2. A treatment method according to the teachings of claim 1 wherein said thermia condition is hypothermia.

3. A treatment method according to the teachings of claim 2 wherein said temperature is above that which is considered normal in a human body.

4. A treatment method according to the teachings of claim 1 wherein said thermia condition is hyperthermia.

5. A treatment method according to the teachings of claim 4 wherein said temperature is below that which is considered normal in a human body.

6. Apparatus for a therapeutic treatment method for use in treating a thermia condition in a human patient, which apparatus comprises a warm water source including a water supply means, a water flow control means, a water heating means, and a thermostat controlling said water heating means, said source connected to an absorbent web for distributing to more than fifty percent of the surface of the body of said human patient a substantially continuous controlled flow of water at a controlled temperature that approximates the temperature that is considered normal in a human body, whereby said flow of water effects sensible heat transfer between said water and said human patient, thereby to ameliorate said thermia condition.

7. The apparatus of claim 6 wherein said equipment further comprises a flexible tube conduit adapted to carry a flow of temperature-controlled water from said water heating means to the proximity of said patient, a system of at least one water-permeable water distribution tube adapted to receive said flow of temperature-controlled water from said conduit and adapted to distribute water over an area of said absorbent web that, by virtue of its absorbency, further distributes said flow of temperature-controlled water throughout the extent thereof and thereby to the close proximity of and wetting said area of the surface of the body of said patient over which said web is draped, thereby to make good thermal contact between said flowing water and said patient.

8. The apparatus described in claim 7 wherein said water source is a refillable reservoir that is elevated with respect to the patient, thereby to provide for water flow by the action of gravity alone.

9. The apparatus described in claim 7 wherein said water source is a water tap connected to the water supply for a building.

10. The apparatus described in claim 7 wherein said water-permeable water distribution tube is a flexible tube having discrete holes through the wall thereof and speced along the length thereof.

11. The apparatus described in claim 7 wherein said water-permeable water distribution tube is a flexible tube having a substantially uniformly porous wall.

12. The apparatus described in claim 7 wherein said water-permeable water distribution tube is attached to a web or sheet that holds said tube in position when draped over said patient.

13. The apparatus described in claim 12 wherein said tube-holding web is separate from said absorbent web that is draped over said patient.

14. The apparatus described in claim 13 wherein said separate tube-holding web is substantially non-permeable, thereby to prevent substantial evaporative cooling of the water applied to the patient.

15. The apparatus described in claim 12 wherein said tube-holding web is also the absorbent web that is draped over said patient.

16. The apparatus described in claim 7 wherein said apparatus further comprises an underlayment upon which said patient is placed, which underlayment to serve the purpose of collecting by gravity said water flow delivered to the body of the patient and to direct said water flow into a spent water receptacle.

17. The apparatus described in claim 16 wherein said underlayment comprises a shallow flexible waterproof tub.

18. The apparatus described in claim 17 wherein said tub has a bottom wall having a top surface thereof adapted by a system of transverse channels to allow water to pass under a patient lying thereupon, thereby to allow for drainage of said spent water from a region surrounding said patient.

19. The apparatus described in claim 17 wherein said tub has a bottom wall having a top surface thereof, said apparatus further comprising a weblike liner to be placed between said top surface and said patient and having a system of transverse channels to allow water to pass under a patient lying thereupon, thereby to allow for drainage of said spent water from a region surrounding said patient.

* * * * *